US007659365B2

(12) United States Patent
Soula et al.

(10) Patent No.: US 7,659,365 B2
(45) Date of Patent: Feb. 9, 2010

(54) TELECHELIC HOMOPOLYAMINO ACIDS FUNCTIONALIZED WITH HYDROPHOBIC GROUPS, AND THEIR APPLICATIONS, ESPECIALLY THERAPEUTIC APPLICATIONS

(75) Inventors: Rémi Soula, Lyons (FR); You-Ping Chan, Lyons (FR); Gérard Soula, Meyzieu (FR); Olivier Breyne, Lyons (FR)

(73) Assignee: Flamel Technologies, Venissieuz (FR)

( * ) Notice: Subject to any disclaimer, the term of this patent is extended or adjusted under 35 U.S.C. 154(b) by 27 days.

(21) Appl. No.: 10/574,475

(22) PCT Filed: Sep. 28, 2004

(86) PCT No.: PCT/FR2004/050465

§ 371 (c)(1), (2), (4) Date: Mar. 21, 2007

(87) PCT Pub. No.: WO2005/033181

PCT Pub. Date: Apr. 14, 2005

(65) Prior Publication Data

US 2007/0265192 A1 Nov. 15, 2007

(30) Foreign Application Priority Data

Oct. 3, 2003 (FR) .................................. 03 50641

(51) Int. Cl.
*C07K 14/00* (2006.01)

(52) U.S. Cl. ....................... 530/324; 530/300; 530/345; 562/571; 562/573; 514/2

(58) Field of Classification Search ..................... 514/2; 530/329, 330, 324, 345; 562/571, 573
See application file for complete search history.

(56) References Cited

U.S. PATENT DOCUMENTS 2,680,749 A 6/1954 Cawley et al.
3,536,672 A 10/1970 Fujimoto et al.
4,126,628 A 11/1978 Paquet
4,321,253 A 3/1982 Beatty
4,351,337 A 9/1982 Sidman
4,443,549 A 4/1984 Sadowski
4,450,150 A 5/1984 Sidman
4,600,526 A 7/1986 Gallot et al.
4,615,697 A 10/1986 Robinson
4,652,441 A 3/1987 Okada et al.
4,661,345 A 4/1987 Tuomanen
4,748,023 A 5/1988 Tamas et al.
4,766,106 A 8/1988 Katre et al.
4,835,293 A 5/1989 Bhatia
4,888,398 A 12/1989 Bichon et al.
4,892,733 A 1/1990 Bichon et al.
4,894,240 A 1/1990 Geoghegan et al.
4,904,479 A 2/1990 Illum
4,976,968 A 12/1990 Steiner
5,023,349 A 6/1991 Bhatia
5,084,278 A 1/1992 Mehta
5,102,872 A 4/1992 Singh et al.
5,204,108 A 4/1993 Illum
5,286,495 A 2/1994 Batich et al.
5,286,497 A 2/1994 Hendrickson et al.
5,399,331 A 3/1995 Loughrey et al.
5,449,513 A 9/1995 Yokoyama et al.
5,510,103 A 4/1996 Yokoyama et al.
5,514,380 A 5/1996 Song et al.
5,534,241 A 7/1996 Torchilin et al.
5,589,455 A 12/1996 Woo
5,609,872 A * 3/1997 Ahlborg et al. .......... 424/185.1
5,656,722 A 8/1997 Dorschug
5,780,579 A 7/1998 Soula et al.
5,834,422 A 11/1998 Balschmidt
5,852,109 A 12/1998 Makino et al.
5,863,900 A 1/1999 Russell-Jones (Continued)

FOREIGN PATENT DOCUMENTS

CA 2068366 11/1992

(Continued)

OTHER PUBLICATIONS

International Search Report mailed Apr. 18, 2005, for No. PCT/FR2004/050465,with English translation.
French Search Report dated Mar. 29, 2004, for No. FR 03-50641.
International Search Report PCT/FR2004/050465, filed Apr. 5, 2005.
Akiyoshi et al., Self-assembled hydrogel nanoparticle of cholesterol-bearing pullulan as a carrier of protein drugs: Complexation and stabilization of insulin, J. Controlled Release 54: 313-320(1998).
Ed. R. Arshady, Micropsheres, Microcapsules and Liposomes; vol. 1 Preparation and Chemical applications, Citrus Books 1999, London.
Ed. J. Senior and M. Radomsky, *Sustained-Release Injectable Products*, Interpharm Press 2000, Denver.
Ed. J. Kreuter, *Colloidal Drug Delivery Systems*, Drugs and the Pharmaceutical Sciences, vol. 66, Marcel Dekker, Inc. 1994, Wilmington.

(Continued)

*Primary Examiner*—David Lukton
(74) *Attorney, Agent, or Firm*—Patton Boggs LLP

(57) ABSTRACT

The invention relates to novel materials based on biodegradable homopolyamino acids and which can be used for the vectorization of (an) active ingredient(s) (AI). The invention also relates to novel pharmaceutical, cosmetic, dietetic or phytosanitaty compositions based on homopolyamino acids. The invention can produce a novel polymer raw material which can be used for the vectoiization of Al that can optimally be: biocompatible, biodegradable, capable of becoming easily associated with a large number of active ingredients or solubilizing them and releasing the active ingredients in vivo. According to the present invention, which primarily relates to linear homopolyamino acids having aspartic or glutamic units and whose attachments can include hydrophobic groups having 8-30 carbon atoms. The homopolymers are amphiphilic and anionic and can easily be transformed at low cost into particles for the vectorization of active ingredients. The particles can form stable aqueous colloidal suspensions.

18 Claims, No Drawings

U.S. PATENT DOCUMENTS 5,869,703 A 2/1999 Kim et al.
5,872,210 A * 2/1999 Medabalimi ................ 530/327
5,876,969 A 3/1999 Fleer et al.
5,904,936 A 5/1999 Huille et al.
5,981,761 A 11/1999 Chou et al.
6,143,314 A 11/2000 Chandrashekar et al.
6,153,193 A 11/2000 Kabanov et al.
6,180,141 B1 1/2001 Lemercier et al.
6,193,953 B1 2/2001 Lohrmann et al.
6,197,535 B1 * 3/2001 Bandyopadhyay et al. .... 435/15
6,201,072 B1 3/2001 Rathi et al.
6,235,282 B1 5/2001 Riviere et al.
6,284,267 B1 9/2001 Aneja
6,309,633 B1 10/2001 Ekwuribe et al.
6,313,095 B1 * 11/2001 Adams et al. ................. 514/18
6,313,260 B2 11/2001 Gruning et al.
6,320,017 B1 11/2001 Ansell
6,500,448 B1 12/2002 Johnson et al.
6,576,254 B1 6/2003 Uchegbu
6,630,171 B1 10/2003 Huille et al.
6,933,269 B2 8/2005 Jordan, IV et al.
6,946,146 B2 9/2005 Mulye
7,030,155 B2 4/2006 Lambert et al.
7,226,618 B1 6/2007 Touraud et al.
7,261,875 B2 8/2007 Li et al.
7,270,832 B2 9/2007 Bryson et al.
2001/0000510 A1 4/2001 Sakurai et al.
2002/0068085 A1 6/2002 Rudnic et al.
2003/0133980 A1 7/2003 Costantino et al.
2004/0038885 A1 2/2004 Bryson et al.
2004/0063628 A1 4/2004 Piccariello et al.
2004/0071716 A1 4/2004 Jansen et al.
2004/0175424 A1 9/2004 Castan et al.
2005/0158392 A1 7/2005 Kim et al.
2006/0099264 A1 5/2006 Chan et al.
2007/0010652 A1 1/2007 Angot et al.
2007/0160568 A1 7/2007 Angot et al.
2007/0178126 A1 8/2007 Angot et al.
2007/0190162 A1 8/2007 Caillol et al.
2007/0196497 A1 8/2007 Pouliquen et al.
2007/0248686 A1 10/2007 Touraud et al.
2007/0254828 A1 11/2007 Dubreucq et al.
2007/0265192 A1 11/2007 Soula et al.
2008/0014250 A1 1/2008 Soula et al.
2008/0015332 A1 1/2008 Bryson et al.
2009/0012028 A1 1/2009 Chan et al.
2009/0110742 A1 4/2009 Constancis et al.

FOREIGN PATENT DOCUMENTS

EP 0 198 769 10/1986
EP 0 179 023 1/1991
EP 0 583 955 2/1994
EP 0 601 508 6/1994
EP 0 721 776 7/1996
EP 0 734 720 10/1996
EP 0 963 758 12/1999
FR 2 732 218 10/1996
FR 2 746 035 9/1997
FR 2 801 226 5/2001
FR 2 838 964 10/2003
FR 2 860 516 10/2003
FR 2 840 614 12/2003
FR 2 843 117 2/2004
FR 2 855 521 12/2004
FR 2 873 040 1/2006
GB 966 760 8/1964
GB 1 024 393 3/1966
GB 1 202 765 8/1970
GB 2 041 517 9/1980
GB 2 240 547 8/1991
WO WO 87/002219 4/1987
WO WO 87/003891 7/1987
WO WO 88/001213 2/1988
WO WO 88/007078 9/1988
WO WO 89/008449 9/1989
WO WO 91/006286 5/1991
WO WO 91/006287 5/1991
WO WO 96/029991 10/1996
WO WO 96/040279 12/1996
WO WO 97/002810 1/1997
WO WO 97/034584 9/1997
WO WO 98/011874 3/1998
WO WO 99/018142 4/1999
WO WO-99/61512 12/1999
WO WO 00/018821 4/2000
WO WO 00/030618 6/2000
WO WO 85/002092 6/2000
WO WO 00/071163 11/2000
WO WO-00/78791 12/2000
WO WO 01/037809 5/2001
WO WO 02/028251 4/2002
WO WO 02/028521 4/2002
WO WO 02/039984 5/2002
WO WO-02/098951 12/2002
WO WO 02/098952 12/2002
WO WO 03/002096 1/2003
WO WO 03/013467 2/2003
WO WO 03/104303 12/2003
WO WO 2004/013206 2/2004
WO WO 2004/060968 7/2004
WO WO 2004/108796 12/2004
WO WO 2005/033181 4/2005
WO WO 2005/051416 6/2005
WO WO 2006/016078 2/2006
WO WO 2007/034320 3/2007
WO WO 2007/116143 10/2007

OTHER PUBLICATIONS

Ed. D.L. Wise, Handbook of Pharmaceutical Controlled Release Technology, Marcel Dekker, Inc. 2000, New York.

Fuller et al., A procedure for the facile synthesis of amino-acid N-carboxyanhydrides, Biopolymers 15: 1869-71 (1976).

Krichekdorf, H.R., Alpha-amino acid N-carboxy anhydride and related heterocycles, Spring Verlag (1987) Berlin.

In the U.S. Patent and Trademark Office, Non-Final Office Action in re: U.S. Appl. No. 08/592,299, dated May. 5, 1997, 3 pages.

In the U.S. Patent and Trademark Office, Non-Final Office Action in re: U.S. Appl. No. 08/592,299, dated Oct. 4, 1996, 6 pages.

In the U.S. Patent and Trademark Office, Final Office Action in re: U.S. Appl. No. 08/621,438, dated Apr. 22, 1998, 1 page.

In the U.S. Patent and Trademark Office, Non-Final Office Action in re: U.S. Appl. No. 08/621,438, dated Feb. 13, 1997,4 pages.

In the U.S. Patent and Trademark Office, Non-Final Office Action in re: U.S. Appl. No. 08/621,438, dated Jul. 24, 1997, 5 pages.

In the U.S. Patent and Trademark Office, Non-Final Office Action in re: U.S. Appl. No. 09/147,032, dated Jul. 6, 1999, 5 pages.

In the U.S. Patent and Trademark Office, Final Office Action in re: U.S. Appl. No. 09/856,378, dated Jan. 28, 2003, 11 pages.

In the U.S. Patent and Trademark Office, Final Office Action in re: U.S. Appl. No. 09/856,378, dated Sept. 27, 2002, 7 pages.

In the U.S. Patent and Trademark Office, Final Office Action in re: U.S. Appl. No. 10/130,783, dated Jan. 27, 2006, 19 pages.

In the U.S. Patent and Trademark Office, Final Office Action in re: U.S. Appl. No. 10/398,133, dated Mar. 24, 2009, 8 pages.

In the U.S. Patent and Trademark Office, Non-Final Office Action in re: U.S. Appl. No. 10/398,133, dated Jun. 13, 2008, 13 pages.

In the U.S. Patent and Trademark Office, Non-Final Office Action in re: U.S. Appl. No. 10/398,133, dated Nov. 4, 2005, 10 pages.

In the U.S. Patent and Trademark Office, Non-Final Office Action in re: U.S. Appl. No. 10/398,133, dated Sept. 28, 2007, 15 pages.

In the U.S. Patent and Trademark Office, Non-Final Office Action in re: U.S. Appl. No. 10/398,134, dated Oct. 17, 2006, 14 pages.

In the U.S. Patent and Trademark Office, Non-Final Office Action in re: U.S. Appl. No. 10/398,134, dated May. 12, 2005, 11 pages.
In the U.S. Patent and Trademark Office, Final Office Action in re: U.S. Appl. No. 10/473,821, dated Dec. 31, 2008, 5 pages.
In the U.S. Patent and Trademark Office, Final Office Action in re: U.S. Appl. No. 10/473,821, dated Jan. 19, 2007, 10 pages.
In the U.S. Patent and Trademark Office, Non-Final Office Action in re: U.S. Appl. No. 10/473,821, dated Aug, 29, 2005, 12 pages.
In the U.S. Patent and Trademark Office, Non-Final Office Action in re: U.S. Appl. No. 10/473,821, dated Mar. 24, 2008, 9 pages.
In the U.S. Patent and Trademark Office, Non-Final Office Action in re: U.S. Appl. No. 10/473,821, dated May. 2, 2006, 8 pages.
In the U.S. Patent and Trademark Office, Final Office Action in re: U.S. Appl. No. 10/516,733, dated Jun. 17, 2008, 9 pages.
In the U.S. Patent and Trademark Office, Non-Final Office Action in re: U.S. Appl. No. 10/516,733, dated Feb. 26, 2009, 4 pages.
In the U.S. Patent and Trademark Office, Non-Final Office Action in re: U.S. Appl. No. 10/516,733, dated Feb. 5, 2007, 7 pages.
In the U.S. Patent and Trademark Office, Non-Final Office Action in re: U.S. Appl. No. 10/516,733, dated Sept. 12, 2007, 7 pages.
In the U.S. Patent and Trademark Office, Final Office Action in re: U.S. Appl. No. 10/558,617, dated Jun. 26, 2009, 14 pages.
In the U.S. Patent and Trademark Office, Final Office Action in re: U.S. Appl. No. 10/558,617, dated Jan. 30, 2008, 8 pages.
In the U.S. Patent and Trademark Office, Non-Final Office Action in re: U.S. Appl. No. 10/558,617, dated Dec. 22, 2008, 8 pages.
In the U.S. Patent and Trademark Office, Non-Final Office Action in re: U.S. Appl. No. 10/558,617, dated Jun. 29, 2007, 10 pages.
In the U.S. Patent and Trademark Office, Non-Final Office Action in re: U.S. Appl. No. 10/580,035, dated Dec. 3, 2008, 25 pages.
In the U.S. Patent and Trademark Office, Non-Final Office Action in re: U.S. Appl. No. 11/509,783, dated Jan. 31, 2008, 9 pages.
In the U.S. Patent and Trademark Office, Non-Final Office Action in re: U.S. Appl. No. 11/601,691, dated Apr. 3, 2009, 29 pages.
In the U.S. Patent and Trademark Office, Non-Final Office Action in re: U.S. Appl. No. 11/878,947, dated Jul. 20, 2009, 11 pages.
Akiyoshi et al., "Stabilization of Insulin upon Supramolecular Complexation with Hydrophobized Polysaccharide Nanoparticle " *Chemistry Letters*, 1995, No. 8, pp. 707-708.
Candau, S., Chapter 3: Light Scattering, *Surfactant Solutions*, vol. 22, Ed. R. Zana, M. Dekker, Inc., NY (1984) pp. 147 -207.
Database WPI Week 200274, AN 2002-685440, Derwent Publications Ltd., London, GB.
Database WPI Week 200275, AN 2002-694010, Derwent Publications Ltd., London, GB.
Database WPI Week 200425, AN 2002-260230, Derwent Publications Ltd., London, GB.
Davis, J.T., "A Quantitative Kinetic Theory of Emulsion Type, I. Physical Chemistry of the Emulsifying Agent," Proceedings of the Second International Congress of Surface Activity, 1957; pp. 426-429.
Forssen et al., *Cancer Res.*, 1983; 43, pp. 546.
Gao et al., *Anal. Chem.*, 1997; 69, pp. 2945.
Griffin, G.C., "Classification of Surface-Active Agents by 'HLB'," *Journal of the Society of Cosmetic Chemists*, 1949; 1:5, pp. 311-327.
Handbook of Chemistry and Physics, 88th Ed., 2008 (Viscosities of Liquids) Section 6, pp. 175-179).
Harada et al., "Formation of Polyion Complex Micelles in an Aqueous Milieu from a Pair of Oppositely-Charged Block Copolymers with Poly(ethylene glycol) Segments," *Macromolecules*, 1995, vol. 28, pp. 5294-5299.
Hoes et al., "Optimization of Macromolecular Prodrugs of the Antitumor Antibiotic Adriamycin," *J. Controlled Release*, 1985; 2, pp. 205-213.
Hudecz et al., "Branched Polypeptides with a POLY-(L-Lysine) Backbone: Synthesis, Conformation, and Immunomodulation," *Polymeric Materials in Medication*, Plenum Press, New York, 1985; pp. 265-289.
Illum et al., "Effect of the Nonionic Surfactant Poloxamer 338 on the Fate and Deposition of Polystyrene Microspheres Following Intravenous Administration," *J. Pharm. Sci.*, 1983; 72:9, pp. 1086-1089.
Jaworek et al., "Effects of Analogs of (pyro)Glu-His-Gly-OH on Food Consumption and Gastric Acid Secretion in Rats," *Life Science*, 1984; 34:26, pp. 2597-2603.
English Abstract for Kataoka, K. "Preparation of Novel Drug Carrier based on the Self-Association of Block Copolymer," Drug Delivery System, 1995, vol. 10, No. 5, pp. 363-370.
Kuroda et al., "Hierarchical Self-Assembly of Hydrophobically Modified Pullulan in Water: Gelation by Networks of Nanoparticles," *Langmuir*, 2002; 18, pp. 3780-3786.
Maa et al., "Spray-Drying of Air-Liquid Interface Sensitive Recombinant Human Growth Hormone," *Journal of Pharmaceutical Sciences*, 1988; 87:2 pp. 152-159.
Mezo et al., "Synthesis and Conformation Studies of Poly(L-Lysine) Based Polypeptides with Ser and Glu/Leu in the Side Chains," *J. Controlled Release*, 2000; 63, pp. 81-95.
Oppenheim et al., "The Primary Structure and Functional Characterization of the Neutral Histidine-Rich Polypeptide from Human Parotid Secretion," *Journal of Biological Chemistry*, 1986; 261:3, pp. 1177-1182.
Regalado et al.,*Macromolecules*, 1999; 32, pp. 8580.
Shen, W.C. , "Acid Sensitive Dissociative Between Poly (Lysine) and Histamine Modified Poly (Glutamate) as a Model for Drug Releasing From Carriers in Endosomes," 1990, *Biochim. Biophys. Acts.*, 1034(1): 122-24.
Tomida et al., *Convenient Synthesis of High Molecular Weight Polv(succinimide) by Acid-Catalysed Pal condensation of L-asiartic Acid*, Polymer, 38: 4733-36 1997.
Tsutsumiuchi et al., "Synthesis of Polyoxazoline-(Glyco)peptide Block Copolymer Ring-opening Polymerization of (Sugar-Substituted) a Amino Acid N-Carboxyanhydrides with Polyoxazoline Macroinitiators," Macromolecules, 1997; 30:4013-17.
Van Heeswijk et al., "The Synthesis and Characterization of Polypeptide-Adriamycin Conjugates and its Complexes with Adriamycin," *J. Controlled Release*, 1985; 1:4, pp. 301-315.
English Summary for Volgler et al., *Helv. Chim. Acta*, 47: 526-544(1964).
Woodle et al., "Sterically Stabilized Liposomes," *Biochim. Biophys. Acta*, 1992; 1113:2, pp. 171-199.
Woodle, M.C., "Controlling Liposome Blood Clearance by Surface-Grafted Polymers," *Adv. Drug Deliv. Rev.*, 1998; 32:1-2, pp. 139-152.

* cited by examiner

TELECHELIC HOMOPOLYAMINO ACIDS FUNCTIONALIZED WITH HYDROPHOBIC GROUPS, AND THEIR APPLICATIONS, ESPECIALLY THERAPEUTIC APPLICATIONS

This application is a 371 of PCT/FR04/50465, filed Sep. 28, 2004, which claims foreign priority to FR 0350641, filed Oct. 3, 2003.

The present invention relates to novel materials based on biodegradable homopolyamino acids that are useful especially for the vectorization of active principle(s) (AP).

The invention further relates to novel pharmaceutical, cosmetic, dietetic or phytosanitary compositions based on these homopolyamino acids. These compositions can be of the type allowing the vectorization of AP and preferably taking the form of emulsions, micelles, particles, gels, implants or films.

The AP in question are advantageously biologically active compounds which can be administered to an animal or human organism by the oral, parenteral, nasal, vaginal, ocular, subcutaneous, intravenous, intramuscular, intradermal, intraperitoneal, intracerebral, buccal or other route.

The AP to which the invention relates more particularly, but without implying a limitation, are proteins, glycoproteins, peptides, polysaccharides, lipopolysaccharides, oligonucleotides or polynucleotides, and organic molecules. However, they can also be cosmetic products or phytosanitary products such as herbicides, insecticides, fungicides, etc.

In the field of the vectorization of active principles, especially medicinal active principles, there is a need in many cases to:

protect them from degradation (hydrolysis, precipitation at the site, enzymatic digestion, etc.) until they reach their site of action, and/or control their rate of release so as to maintain a therapeutic level over a defined period, and/or transport them (with protection) to the site of action.

For these purposes, several types of polymers have been studied and some are even commercially available. Examples which may be mentioned are polymers of the polylactic, polylactic-glycolic, polyoxyethylene-oxypropylene, polyamino acid or polysaccharide type. These polymers constitute starting materials for the manufacture of e.g. mass implants, microparticles, nanoparticles, vesicles, micelles or gels. In addition to the fact that these polymers have to be suitable for the manufacture of such systems, they must also be biocompatible, non-toxic, non-immunogenic and economic and they must be easy to eliminate from the body and/or biodegradable. On this last point, it is further essential that biodegradation in the organism generates non-toxic products.

Various patents, patent applications or scientific articles are referred to below in order to illustrate the prior art relating to polymers employed as starting materials for the production of AP vectorization systems.

Patent U.S. Pat. No. 4,652,441 describes polylactide microcapsules encapsulating the hormone LH-RH. These microcapsules are produced by preparing a water-in-oil-in-water emulsion and comprise an aqueous inner layer containing the hormone, a substance (gelatin) for fixing the latter, an oily polylactide layer and an aqueous outer layer (polyvinyl alcohol). The AP can be released over a period of more than two weeks after subcutaneous injection.

Patent U.S. Pat. No. 6,153,193 describes compositions based on amphiphilic poly(oxyethylene)-poly(oxypropylene) micelles for the vectorization of anticancer agents such as adriamycin.

Akiyoshi et al. (J. Controlled Release 1998, 54, 313-320) describe pullulans which are hydrophobized by the grafting of cholesterol and form nanoparticles in water. These nanoparticles, which are capable of complexing reversibly with insulin, form stable colloidal suspensions.

Patent U.S. Pat. No. 4,351,337 describes amphiphilic copolyamino acids based on leucine and glutamate which can be used in the form of implants or microparticles for the controlled release of active principles. The latter can be released over a very long period that depends on the rate of degradation of the polymer.

Patent U.S. Pat. No. 4,888,398 describes polymers based on polyglutamate or polyaspartate, and optionally polyleucine, with pendent groups of the alkoxy-carbonylmethyl type randomly located along the polyamino acid chain. These polyamino acids, grafted with side groups, e.g. methoxycarbonylmethyl groups, can be used in the form of prolonged-release biodegradable implants containing an AP.

Patent U.S. Pat. No. 5,904,936 describes nanoparticles obtained from a polyleucine-polyglutamate block polymer which are capable of forming stable colloidal suspensions and of associating spontaneously with biologically active proteins without denaturing them. The latter can then be released in vivo in a controlled manner over a long period.

Patent U.S. Pat. No. 5,449,513 describes amphiphilic block copolymers comprising a polyoxyethylene block and a polyamino acid block, for example poly(beta-benzyl-L-aspartate). These polyoxyethylene-polybenzylaspartate polymers form micelles capable of encapsulating hydrophobic active molecules such as adriamycin or indomethacin.

Patent application WO-A-99/61512 describes polylysines and polyornithines functionalized with a hydrophobic group (palmitic acid joined to the polylysine or polyornithine) and a hydrophilic group (polyoxyethylene). In the presence of cholesterol, these polymers, e.g. polylysine grafted with polyoxyethylene and palmitoyl chains, form vesicles capable of encapsulating doxorubicin or DNA. These polymers based on polylysines are cationic in a physiological medium.

Patent application WO-A-00/30618 in the name of the Applicant describes poly(sodium glutamate)-poly(methyl, ethyl, hexadecyl or dodecyl glutamate) block or random polymers capable of forming stable colloidal suspensions and of associating spontaneously with biologically active proteins without denaturing them. The latter can then be released in vivo in a controlled manner over a long period. These amphiphilic copolyamino acids are modified by the presence of a hydrophobic alkyl side chain. These alkyl groups are covalently grafted onto the polymer via an ester group. These polymers are anionic in a physiological medium.

This prior art relating to vectorization systems includes a number of references concerning hydrophilic polymers that contain hydrophobic groups at the end of chains.

Patent FR 2 533 209 describes lipopeptides consisting of a hydrophobic chain containing 8 to 24 carbon atoms and a hydrophilic or hydrophilized peptide chain. These products are useful especially as emulsifiers or liquid crystals.

The following may be cited within the same spirit and in the technical field of liposomes:

Patent application WO-A-02/098951, which describes polyamino acids or certain derivatives thereof having a lipid group at one of the two chain ends. These can be e.g. poly(gamma-L-benzyl-L-glutamate) or poly(N-(2-hydroxy-ethyl)-L-glutamine) carrying a heptadecyloctadecylamine terminal group. These polymers are useful for the preparation of liposomes.

Patent U.S. Pat. No. B-5,534,241 discloses amphiphilic compounds consisting of polylysine residues substituted in the chain by chelating radicals of the diethylenetriaminepentaacetic acid type, and at one end of the chain by a lipophilic group formed of N-glutarylphosphatidylethanolamine (NGPE). These compounds are intended for incorporation into the bilayer membrane of liposomes.

The same applies to the amphiphilic polymers described in patent U.S. Pat. No. B1-6,284,267. These amphiphilic polymers are linear, branched or stellate hydrophilic polymers having at least two hydrophobic groups bonded to their ends. Said patent relates essentially to neutral hydrophilic polymers based on polyethylene glycol, as evidenced by all the Examples in said patent. Now, this type of polymer is not biodegradable, which constitutes a major disadvantage. Consequently, said patent neither describes nor even suggests the use of an anionic linear polyamino acid, such as a polyglutamate or polyaspartate, as a hydrophilic polymeric part of a telechelic amphiphilic polymer.

Thus, although there are a very large number of technical solutions in the prior art which have been developed and proposed for the vectorization of medicinal active principles, it is difficult to find an answer to all the demands and the situation remains unsatisfactory. More specifically, it has been possible to identify an unsatisfied need for a biodegradable material for producing particles for the vectorization of active principles, said material being capable of forming an aqueous suspension of vectorizing nanoparticles or microparticles suitable for associating reversibly with active principles.

In this context, one of the essential objects of the present invention is to provide novel linear, amphiphilic polyamino acids which are anionic at animal physiological pH (e.g. in the order of 7.4) and which represent an improvement compared with those described in patent FR-A-2 533 209 or patent U.S. Pat. No. B1-6,284,267, especially in terms of protein association capacity and biodegradability.

Another essential object of the present invention is that these polymers are capable of being used for the vectorization of AP and make it possible optimally to satisfy all the specifications of the specifications sheet, namely, in particular:

capacity:
- easily and economically to form stable aqueous colloidal suspensions,
- easily to associate with numerous active principles
- and to release these active principles in vivo, biocompatibility, biodegradability, stability to hydrolysis This and other objects are achieved by the present invention, which relates first and foremost to an anionic, linear, amphiphilic homopolyamino acid, characterized in that its two ends carry hydrophobic groups that are identical to or different from one another, and in that it can be symbolized by the following schematic general formula:

HG-X-PAA-Y-HG in which:

- HG is a hydrophobic group,
- X and Y independently are a link corresponding to a covalent bond or to a polyvalent radical derived from a chemical entity different from the precursor of HG, and
- PAA is an anionic, hydrophilic homopolyamino acid chain.

It is to the Applicant's credit to have had the idea of combining, in a totally judicious and advantageous manner, specific anionic, biodegradable, linear homopolyamino acids (e.g. polyAsp or polyGlu) with hydrophobic groups located at the ends of the PAA chain.

These novel amphiphilic homopolymers have proved particularly suitable for the vectorization of proteins.

As defined in the invention:

- the term "homopolyamino acid" covers on the one hand PAA containing a single type of "amino acid" unit (e.g. either glutamic or glutamate units or aspartic or aspartate units) and on the other hand not only oligoamino acids containing from 2 to 20 "amino acid" units, but also homopolyamino acids containing more than 20 "amino acid" units;
- the term "amino acid unit" refers to a monomeric or non-monomeric unit formed of a skeleton of a given amino acid, irrespective of the substituents, provided that they do not modify the nature of the amino acid in question.

These homopolymers have surprising properties of association and/or encapsulation with one or more active principles, compared with analogous products.

Furthermore, they are easily degraded in the presence of enzymes to non-toxic catabolites/metabolites (amino acids).

As defined in the invention and throughout the present disclosure, the terms "association" or "associate" employed to qualify the relationships between one or more active principles and the homopolyamino acids denote in particular that the active principle(s) is (are) bonded to the homopolyamino acid(s) especially by a weak bond, e.g. by ionic bonding and/or hydrophobic contact, and/or are encapsulated by the homopolyamino acid(s).

Preferably, the homopolyamino acids according to the present invention are homooligomers or homopolymers comprising alpha-L-glutamate and/or alpha-L-glutamic units or alpha-L-aspartate and/or alpha-L-aspartic units.

The hydrophobic groups HG are advantageously and judiciously selected from the group comprising:

- linear or branched C8 to C30 alkyls which can optionally contain at least one unit of unsaturation and/or at least one heteroatom,
- C8 to C30 alkylaryls or arylalkyls which can optionally contain at least one unit of unsaturation and/or at least one heteroatom,
- and C8 to C30 (poly)cyclic groups which can optionally contain at least one unit of unsaturation and/or at least one heteroatom.

In the case where the links X and Y are direct covalent bonds, the precursors of HG are selected in practice, without implying a limitation, from the group comprising alcohols, carboxylic acids and amines, it being possible for these compounds easily to be functionalized by those skilled in the art.

The HG are then bonded to the PAA ends by amide, ester, carbonate, carbamate or urea linkages.

In the case where the links X and Y are polyvalent (e.g. divalent) radicals derived from a chemical entity different from the precursor of HG, the precursors of HG are preferably selected from the same species as in the case where X and Y are a direct covalent bond.

This time, however, the HG form a covalent bond with the link (or spacer radical) X, Y and are not directly joined to the PAA ends.

X, Y is thus a bridge joining HG on the one hand to a PAA end on the other.

X and Y are independently selected from radicals derived from functional compounds that are capable of reacting with the functional group (s) of HG and the N-terminal and C-terminal groups of the PAA part. These functional compounds can advantageously belong to the group comprising "amino acid" units different from the constituent monomeric unit of the PAA homopolymer part, amino alcohols, diamines, diacids, diols and hydroxy acids.

Whatever the case may be, the chemical linkages PAA-(X or Y) and (X or Y)-HG are also preferably amide, ester, carbonate, carbamate or urea linkages.

In one preferred embodiment of the invention, the homopolyamino acid has one of the general formulae (I), (II) and (III) below:

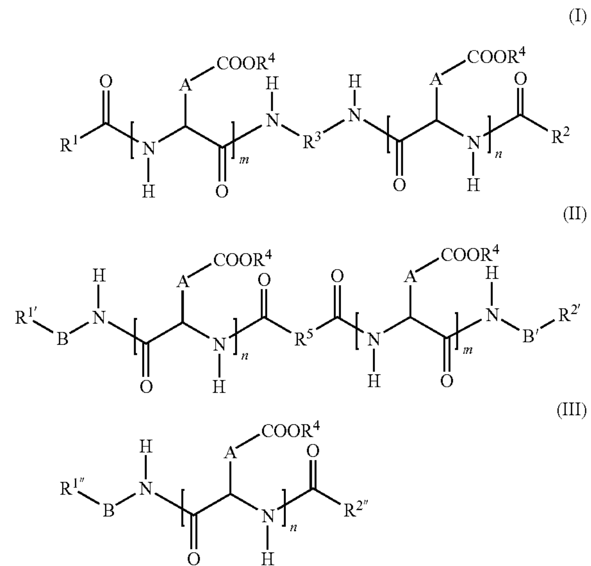

in which $R^1CO$—, $R^2CO$—, $R^{1'}$, $R^{2'}$, $R^{1''}$ and $R^{2''}$. independently are a C8 to C30 hydrophobic group $R^3$ is a linear C2 to C6 alkyl group;

$R^4$ is H or a cationic entity preferably selected from the group comprising:

metal cations advantageously selected from the subgroup comprising sodium, potassium, calcium and magnesium, organic cations advantageously selected from the subgroup comprising:

cations based on amine, cations based on oligoamine, cations based on polyamine (polyethylenimine being particularly preferred), and cations based on amino acid(s) and advantageously selected from the class comprising cations based on lysine or arginine; and cationic polyamino acids advantageously selected from the subgroup comprising polylysine and oligolysine;

$R^5$ is a C2 to C6 alkyl, dialkoxy or diamine group;

A independently is $—CH_2—$ (aspartic unit) or $—CH_2—CH_2—$ (glutamic unit);

B is a link formed of a direct covalent bond or an amino acid residue of the formula below:

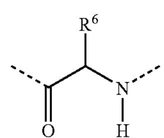

in which $R^6$ is a radical characteristic of a natural amino acid and preferably selected from the group comprising H (in which case B is a glycine residue), methyl (in which case B is an alanine residue), isobutyl (in which case B is a leucine residue), isopropyl (in which case B is a valine residue) and $CH_2Ph$ (in which case B is a phenylalanine residue); and n+m is defined as the degree of polymerization and varies from 3 to 1000, preferably between 20 and 300.

Particularly preferably, the hydrophobic groups $R^1CO$—, $R^2CO$—, $R^{1'}$, $R^{2'}$, $R^{1''}$ and $R^{2''}$ are:

linear or branched C8 to C30 alkyl groups which can optionally contain at least one unit of unsaturation and/or at least one heteroatom, C8 to C30 alkylaryl or arylalkyl groups which can optionally contain at least one unit of unsaturation and/or at least one heteroatom, or C8 to C30 (poly)cyclic groups which can optionally contain at least one unit of unsaturation and/or at least one heteroatom.

In practice the hydrophobic group HG is e.g. a group selected from the group comprising the following species: palmitate, stearate, cholesteryl and tocopheryl.

According to another definition, the homopolyamino acids according to the invention have a molecular weight of between 2000 and 100,000 g/mol, preferably of between 5000 and 40,000 g/mol.

Remarkably, the homopolyamino acids of the invention can be used in several ways, depending on the nature of the hydrophobic groups and the degree of polymerization of the homopolyamino acid. The methods of forming a polymer for the encapsulation of an active principle in the various forms envisaged by the invention are known to those skilled in the art. For further details, reference may be made e.g. to the following few references of particular pertinence:

"*Microspheres, Microcapsules and Liposomes;* vol 1. *Preparation and chemical applications*" Ed. R. Arshady, Citus Books 1999. ISBN: 0-9532187-1-6.

"*Sustained-Release Injectable Products*" Ed. J. Senior and M. Radomsky, Interpharm Press 2000. ISBN: 1-57491-101-5.

"*Colloidal Drug Delivery Systems*" Ed. J. Kreuter, Marcel Dekker, Inc. 1994. ISBN: 0-8247-9214-9.

"*Handbook of Pharmaceutical Controlled Release Technology*" Ed. D. L. Wise, Marcel Dekker, Inc. 2000. ISBN: 0-8247-0369-3.

These homopolyamino acids are also extremely valuable in that, depending on the length of the homopolymer (degree of polymerization) and the nature of the hydrophobic groups, they disperse in water at pH 7.4 (e.g. with a phosphate buffer) to give colloidal solutions or suspensions or structured or non-structured gels, depending on the homopolymer concentration. Furthermore, the polyamino acids (in particulate or non-particulate form) can encapsulate or easily associate with active principles such as proteins, peptides or small molecules. The preferred forming method is the one described in patent application WO-A-00/30618 in the name of the Applicant, which consists in dispersing the homopolymer in water and incubating the solution in the presence of an AP. This colloidal solution of vectorization particles consisting of the homopolyamino acids according to the invention can then be filtered on a 0.2 μm filter and then directly injected into a patient.

When the hydrophilic/hydrophobic ratio decreases, the homopolymer can then form microparticles capable of associating with or encapsulating AP. In this context the microparticles can be formed by cosolubilizing the AP and the homopolymer in an appropriate organic solvent and then precipitating the mixture in water. The particles are subsequently recovered by filtration and can then be used for oral administration (in the form of gelatin capsules, in compacted and/or coated form, or else in the form of a dispersion in an oil) or for parenteral administration after redispersion in water.

In one variant the homopolymer can be solubilized in a biocompatible solvent such as N-methylpyrrolidone, or an appropriate oil such as Mygliol®, and then injected by the intramuscular or subcutaneous route or into a tumor. Diffusion of the solvent or oil leads to precipitation of the homopolymer at the injection site and thus forms a depot. These depots then ensure a controlled release by diffusion and/or by erosion and/or by hydrolytic or enzymatic degradation of the homo-polymer.

Independently of the fact that the microparticulate form of the homopolyamino acid according to the invention is preferred, the homopolymers of the invention, in neutral or ionized form, can more generally be used by themselves or in a liquid, solid or gel composition and in an aqueous or organic medium.

It should be understood that the homopolymer based on polyamino acids contains carboxyl groups which are either neutral (COOH form) or ionized ($COO^-$ anion), depending on the pH and the composition. For this reason the solubility in an aqueous phase is a direct function of the proportion of free COOH in the homopolymer (not grafted with the hydrophobic unit) and of the pH. In aqueous solution the countercation can be a metal cation such as sodium, calcium or magnesium, or an organic cation such as triethanolamine, tris(hydroxymethyl)-aminomethane or a polyamine like polyethylenimine.

The homopolymers of the invention are obtained e.g. by methods known to those skilled in the art. It is pointed out first of all that, to obtain a polyamino acid of the alpha type, the most common technique is based on the polymerization of amino acid N-carboxy anhydrides (NCA), which is described e.g. in the article "*Biopolymers*" 1976, 15, 1869, and in the work by H. R. Kricheldorf entitled "*Alpha-amino acid N-carboxy anhydride and related heterocycles*" Springer Verlag (1987). The NCA derivative is preferably NCA-Glu-O-Bz (Bz=benzyl) because the benzyl group can be selectively hydrolyzed without affecting other chemical functional groups of the homopolymers or of the hydrophobic group.

By way of example, a homopolymer of general structure (I) can be obtained especially according to the scheme below (where $R_1$=$R_2$=stearate group, $R_3$=—$(CH_3)_2$— and the polyamino acid is a polyglutamate):

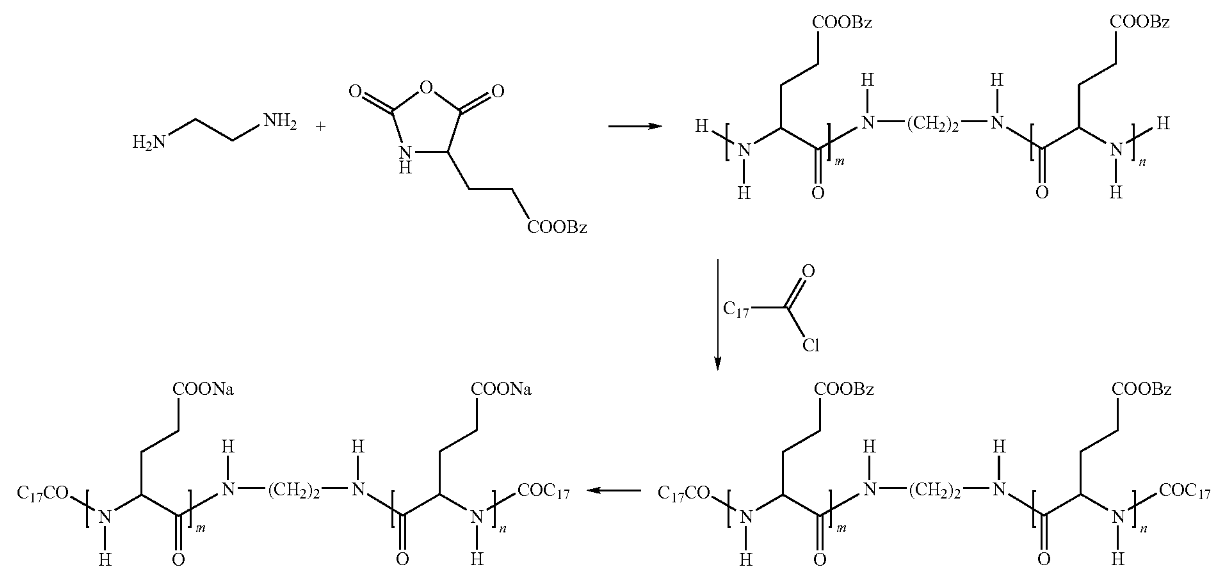

A homopolymer of structure (II) can be obtained especially by the following reaction sequence: initiation of a polymerization of NCA-Glu-O-Bz by a hydrophobic group carrying an amine group to give an intermediate (II-A) with a terminal amine group, followed by coupling of the intermediate (II-A) with an appropriate difunctional compound such as an acid dichloride, a diisocyanate or a dichloroformate.

A homopolymer of structure (III) can in turn be obtained especially by reacting the intermediate (II-A) with a functionalized hydrophobic group such as an acid chloride or a chloroformate.

By way of example, an intermediate compound of the type (II-A) can be obtained especially according to the following scheme ($R^{1'}$ is dodecanol and B is leucine):

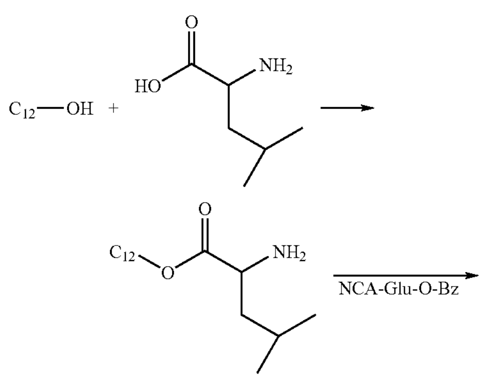

-continued

It must be noted that the degree of polymerization is defined by the molar ratio of the . . . initiator to that of monomer.

According to another of its features, the invention relates to a pharmaceutical, cosmetic, dietetic or phytosanitary composition comprising at least one homopolyamino acid as defined above and optionally at least one active principle, which can be a therapeutic, cosmetic, dietetic or phytosanitary active principle.

According to one valuable provision of the invention, the active principle is associated with the homopolyamino acid(s) by one or more bonds other than covalent chemical bonds.

The techniques of associating one or more AP with the grafted homopolyamino acids according to the invention are described in particular in patent application WO-A-00/30618. They consist in incorporating at least one active principle into the liquid medium containing particles VP to give a colloidal suspension of VP laden or associated with one or more active principles AP. This incorporation, which results in the AP being trapped by the VP, can be effected in the following manner:

- the introduction of AP into aqueous solution, followed by the addition of VP, either in the form of a colloidal suspension or in the form of isolated VP (lyophilizate or precipitate); or
- the addition of AP, either in solution or in the pure or preformulated state, to a colloidal suspension of particles VP, optionally prepared for immediate use by the dispersion of dry VP in an appropriate solvent such as water.

Preferably, the active principle is a protein, a glycoprotein, a protein bonded to one or more polyalkylene glycol chains (preferably polyethylene glycol (PEG) chains: "PEGylated protein"), a polysaccharide, a liposaccharide, an oligo-nucleotide, a polynucleotide or a peptide.

In one variant, the active principle is a "small" hydrophobic, hydrophilic or amphiphilic organic molecule.

As defined in the present disclosure, a "small" molecule is especially a small non-protein molecule.

The following may be mentioned as examples of AP that can be associated with the homopolyamino acids according to the invention, whether or not they are in the form of nanoparticles or microparticles:

- proteins such as insulin, interferons, growth hormones, interleukins, erythropoietin or cytokines;
- peptides such as leuprolide or cyclosporin;
- small molecules such as those belonging to the anthracycline, taxoid or camptothecin family;
- and mixtures thereof.

In one embodiment the composition of the invention is in the form of a gel, a solution, a suspension, an emulsion, micelles, nanoparticles, microparticles, an implant, a powder or a film.

In one of its particularly preferred forms, the composition, whether or not laden with active principle(s), is a stable colloidal suspension of nanoparticles and/or microparticles and/or micelles of homopolyamino acids in an aqueous phase.

In another embodiment the composition of the invention is in the form of a solution in a biocompatible solvent and can be injected by the subcutaneous or intramuscular route or into a tumor.

If the composition according to the invention is a pharmaceutical composition, it can be administered by the oral, parenteral, nasal, vaginal, ocular, subcutaneous, intravenous, intramuscular, intradermal, intraperitoneal, intracerebral or buccal route.

It is also possible to envisage a composition in the form of a solution in a biocompatible solvent that can be injected by the subcutaneous or intramuscular route or into a tumor.

In another variant the composition according to the invention is formulated in such a way that it is capable of forming a depot at the injection site.

The invention further relates to compositions which comprise homo-polyamino acids according to the invention and active principles and which can be used for the preparation of:

- drugs, particularly for administration by the oral, nasal, vaginal, ocular, subcutaneous, intravenous, intramuscular, intradermal, intraperitoneal or intracerebral route, it being possible in particular for the active principles of these drugs to be proteins, glycoproteins, proteins bonded to one or more polyalkylene glycol chains {e.g. polyethylene glycol (PEG) chains, in which case the term "PEGylated" proteins is used}, peptides, polysaccharides, liposaccharides, oligonucleotides, polynucleotides and small hydrophobic, hydrophilic or amphiphilic organic molecules;
- and/or nutriments;
- and/or cosmetic or phytosanitary products.

According to yet another of its features, the invention relates to a process for the preparation of:

- drugs, particularly for administration by the oral, nasal, vaginal, ocular, subcutaneous, intravenous, intramuscular, intradermal, intraperitoneal or intracerebral route, it being possible in particular for the active principles of these drugs to be proteins, glycoproteins, proteins bonded to one or more polyalkylene glycol chains {e.g. polyethylene glycol (PEG) chains, in which case the term "PEGylated" proteins is used}, peptides, polysaccharides, liposaccharides, oligonucleotides, polynucleotides and small hydrophobic, hydrophilic or amphiphilic organic molecules;
- and/or nutriments;
- and/or cosmetic or phytosanitary products, said process being characterized in that it consists essentially in using at least one homopolyamino acid as defined above and/or the composition also described above.

The invention further relates to a method of therapeutic treatment that consists essentially in administering the composition as described in the present disclosure by the oral, parenteral, nasal, vaginal, ocular, subcutaneous, intravenous, intramuscular, intradermal, intraperitoneal, intracerebral or buccal route.

In one particular variant of the invention, said method of therapeutic treatment consists essentially in converting the composition as described above to a solution in a biocompatible solvent and then injecting it by the subcutaneous or intramuscular route or into a tumor, preferably in such a way that it forms a depot at the injection site.

The invention will be better understood and its advantages and variants will become clearly apparent from the Examples below, which describe the synthesis of the telechelic homopolyamino acids, their conversion to an AP vectorization system (stable aqueous colloidal suspension) and the demonstration of the ability of such a system to associate with a protein to form pharmaceutical compositions.

EXAMPLE 1

Synthesis of a t-pGluONa C18/C18

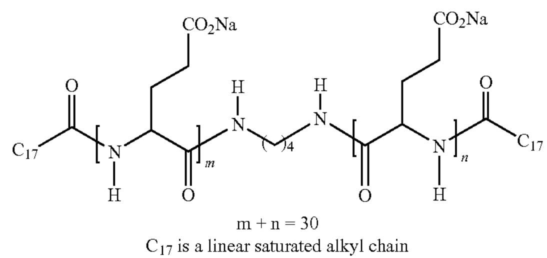

m + n = 30
$C_{17}$ is a linear saturated alkyl chain

Step 1: Polymerization

In a 1 l reactor under a stream of nitrogen, 39.5 g of NCA GluOBz are dissolved in 495 ml of NMP at 40° C. 0.33 g of 1,4-butanediamine is solubilized in 5 ml of NMP and then added to the reaction medium. The polymerization is stopped at 90% NCA conversion by the addition of HCl (4 M in dioxane, 5.0 ml). The polymer is precipitated in a methanol/diisopropyl ether mixture (700/2800 ml), filtered off and then washed with methanol (2×1 l) and diisopropyl ether (2×1 l). Finally, the product is dried in an oven under vacuum at 40° C. to give 10.8 g of the telechelic polymer t-pGluOBz.2HCl.

The number-average molecular weight (Mn) (determined by GPC) is 4.5 kg/mol in PMMA equivalents.

Step 2: Grafting of the Terminal Amines 6 g of the above polymer are then dissolved in 300 ml of THF at room temperature. This solution is cooled to 0° C. prior to the addition of palmitoyl chloride (0.89 g). Finally, 0.47 g of triethylamine is added. The medium is then brought back to room temperature for one hour. When the reaction has ended, the reaction medium is poured into 2.1 l of diisopropyl ether. The precipitate is filtered off and washed with 96% ethanol (3×300 ml) and then with diisopropyl ether (3×300 ml). Finally, the product is dried in an oven under vacuum at 40° C. to give 6.3 g of the polymer t-pGluOBz-C18.

The Mn (determined by GPC NMP) is 6.1 kg/mol in PMMA equivalents.

Step 3: Hydrolysis of the Benzyl Esters 6 g of the above polymer are dissolved in 46 ml of TFA at room temperature. The solution is then cooled to 0° C. prior to the dropwise addition of HBr (30% by weight in acetic acid, 20.6 ml, i.e. 4 equivalents). When the addition has ended, the medium is stirred for 4 hours at room temperature. The end of the reaction is checked by $^1$H NMR of the reaction medium in TFA-d. The reaction medium is then poured into a water/diisopropyl ether mixture (50/50, total volume of 324 ml). The polymer is then filtered off on a frit and washed with diisopropyl ether (3×100 ml). The polymer is dried for 48 h at 40° C. under vacuum to give 3.3 g of the polymer.

The presence of the hydrophobic groups grafted onto the ends of the polymer is confirmed by $^1$H NMR in TFA-d and the degree of polymerization is 30 (the nominal value is 30). The Mn (determined by GPC NMP) is 6.1 kg/mol in PMMA equivalents.

Step 4: Suspension of the Polymer in Water 2.7 g of the above polymer are suspended in 100 ml of demineralized water. 21 ml of 1 N NaOH solution are added slowly. The neutralization has ended when all the polymer has solubilized and the pH is around 7.4. The solution obtained is clear to the eye and stable over time at room temperature.

EXAMPLE 2

Synthesis of a t-pGluONa PheOC12/C12

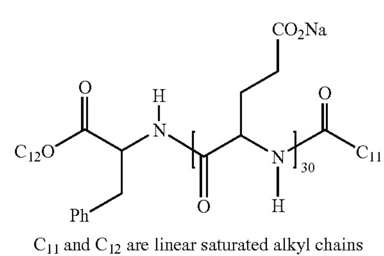

$C_{11}$ and $C_{12}$ are linear saturated alkyl chains

Step 1: Polymerization 192 ml of NMP are heated to 40° C. in a 500 ml reactor under nitrogen. 60 g of NCA GluOBz are then dissolved in this solvent. When the mixture is homogeneous, a solution of the initiator in NMP (2.28 g of PheOC12 in 25 ml at 40° C.) is introduced into the reaction medium. The reaction is followed by IR in order to estimate the NCA conversion. At 90% the reaction is stopped by the addition of excess HCl (4 M in dioxane, 4.27 ml). The reaction medium is then run slowly into 4.5 l of water. The precipitated polymer is subsequently filtered off and washed with acidic methanol (2×310 ml) and then with diisopropyl ether (2×310 ml). Finally, the product is dried in an oven under vacuum at 40° C. to give 39.9 g of the polymer pGluOBz-PheOC12 (i.e. a yield of 88%).

The Mn (determined by GPC NMP) is 12.5 kg/mol in PMMA equivalents.

Step 2: Grafting of the Terminal Amine 10 g of the above polymer are then dissolved in 361 ml of THF at room temperature. This solution is cooled to 0° C. prior to the addition of lauroyl chloride diluted in THF (0.66 g in 7 ml of THF). Finally, 0.5 ml of triethylamine is added. The medium is then brought back to room temperature for a reaction time of one hour. The rapid formation of a precipitate of triethylamine hydrochloride is observed. When the reaction has ended, the reaction medium is poured into 1.4 l of diisopropyl ether. The precipitate is filtered off and washed with 96% ethanol (2×360 ml) and then with diisopropyl ether (2×360 ml). Finally, the product is dried in an oven under vacuum at 40° C. to give 9.5 g of the polymer t-pGluOBz-PheOC12/C12.

The Mn (determined by GPC NMP) is 11.9 kg/mol in PMMA equivalents.

Step 3: Hydrolysis of the Benzyl Esters 8.9 g of the above polymer are dissolved in 68 ml of TFA at room temperature. The solution is then cooled to 0° C. prior to the dropwise addition of HBr (30% by weight in acetic acid, 30 ml, i.e. 4 equivalents). When the addition has ended, the medium is stirred for 4 hours at room temperature. The end of the reaction is checked by $^1$H NMR of the reaction medium in TFA-d. The reaction medium is then poured into a water/diisopropyl ether mixture (50/50, total volume of 480 ml).

The polymer is then filtered off on a frit and washed with ethanol (2×100 ml) and then with diisopropyl ether (2×135 ml). The polymer is dried for 48 h at 40° C. under vacuum to give 4.93 g of the polymer t-pGluOH-PheOC12/C12 (i.e. a yield of 90%).

The presence of the hydrophobic groups grafted onto the ends of the polymer is confirmed by $^1$H NMR in TFA-d and the degree of polymerization is 36 (the nominal value is 30). The Mn (determined by GPC NMP) is 10.0 kg/mol in PMMA equivalents.

Step 4: Suspension of the Polymer in Water 4.4 g of the above polymer are suspended in 150 ml of demineralized water. 31 ml of 1 N NaOH solution are added slowly. The neutralization has ended when all the polymer has solubilized and the pH is around 7.4. The solution obtained is clear to the eye and stable over time at room temperature.

EXAMPLE 3

Synthesis of a t-pGluONa PheOC18/C18

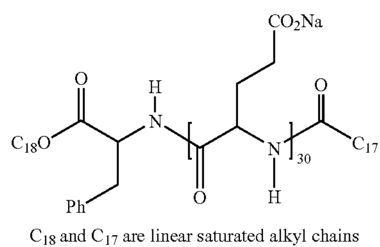

$C_{18}$ and $C_{17}$ are linear saturated alkyl chains

This polymer was synthesized by the same process as that described in Example 2. The degree of polymerization, determined by $^1$H NMR in TFA-d, is 38 (the nominal value is 30). The Mn (determined by GPC NMP) is 7.0 kg/mol in PMMA equivalents.

EXAMPLE 4

Synthesis of a t-pGluONa PheOC18/T

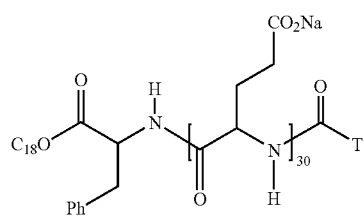

$C_{18}$ is a linear saturated alkyl chain and T is D,L-alpha-tocopherol

This polymer was synthesized by the same process as that described in Example 2. The grafting of the D,L-alpha-tocopherol group is effected by reaction with the corresponding chloroformate derivative. The degree of polymerization, determined by $^1$H NMR in TFA-d, is 36 (the nominal value is 30). The Mn (determined by GPC NMP) is 7.6 kg/mol in PMMA equivalents.

EXAMPLE 5

Synthesis of a Comparative Compound C1, pGluONa C18

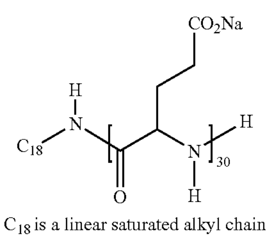

$C_{18}$ is a linear saturated alkyl chain

This polymer is obtained by a synthesis equivalent to that reported in Example 2. The initiator employed in this case is stearylamine and no grafting reaction is effected at the other end of the polymer. At the end of the synthesis, the polymer has the following characteristics:

The degree of polymerization, determined by $^1$H NMR in TFA-d, is 32 (the nominal value is 30). The Mn (determined by GPC NMP) is 8.300 kg/mol in PMMA equivalents.

EXAMPLE 6

Study of Association with Insulin

An aqueous solution of pH 7.4 containing 10 mg of polymer per milliliter and 200 IU of insulin (7.4 mg) is prepared. The solutions are incubated for two hours at room temperature and the free insulin is separated from the associated insulin by ultrafiltration (cut-off at 100 kDa, 15 minutes under 10,000 G at 18° C.). The free insulin recovered from the filtrate is then measured quantitatively by HPLC (high performance liquid chromatography) and the amount of associated insulin is deduced. The results are given in Table 1 below.

TABLE 1

| Polymer | % association |
|---|---|
| Ex. 3 | 93% |
| Ex. 4 | 96% |
| Ex. 5 (C1) | 37% |

The results demonstrate that the polymers of the invention are capable of associating with insulin to give colloidal suspensions with a size greater than 100 kDa and that the association capacities with insulin are very high. The association capacity of these polymers makes them suitable for use as vectorizing agents.

The invention claimed is:

1. An anionic, linear, amphiphilic homopolyamino acid, wherein its two ends carry hydrophobic groups that are identical to or different from one another; and having one of the general formulae (I), (II), and (III) below:

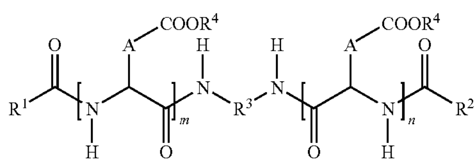

wherein n+m is defined as the degree of polymerization and varies from 3 to 1000;

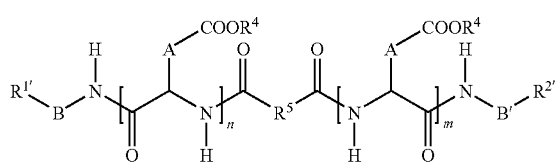

wherein n+m is defined as the degree of polymerization and varies from 3 to 1000;

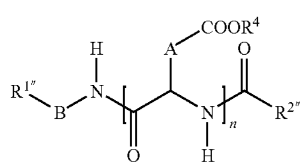

wherein n is defined as the degree of polymerization and varies from 3 to 1000;

and wherein:

$R^1CO$—, $R^2CO$—, $R^{1'}$, $R^{2'}$, $R^{1''}$ and $R^{2''}$ independently are a C8 to C30 hydrophobic group;

$R^3$ is a linear C2 to C6 alkyl group;

$R^4$ is selected from the group consisting of H, a metal cation, an organic cation, a cation based on amino acid(s), and a cationic polyamino acid;

$R^5$ is a C2 to C6 alkyl, dialkoxy or diamine group;

A independently is —$CH_2$-or —$CH_2$—CH2—; and

B is a link formed of a direct covalent bond or an amino acid residue of the formula below:

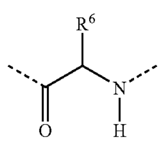

wherein R is a radical characteristic of a natural amino acid and selected from the group consisting of H (in which case B is a glycine residue), methyl (in which case B is an alanine residue), isobutyl (in which case B is a leucine residue), isopropyl (in which case B is a valine residue) and $CH_2Ph$ (in which case B is a phenylalanine residue).

2. The homopolyamino acid according to claim 1, having a molecular weight between 2000 and 100,000 glmol.

3. The pharmaceutical, cosmetic, dietetic or phytosanitary composition comprising at least one homopolyamino acid according to claim 1.

4. The composition according to claim 3, said composition comprising at least one active principle.

5. The composition according to claim 4, wherein the active principle is associated with the homopolyamino acid by one or more bonds other than covalent chemical bonds.

6. The composition according to claim 4, wherein the active principle is selected from the group consisting of: a protein, a glycoprotein, a protein bonded to one or more polyalkylene glycol chains, a protein bonded to polyethylene glycol (PEG) chains, a polysaccharide, a liposaccharide, an oligonucleotide, a polynucleotide and a peptide.

7. The composition according to claim 4, wherein the active principle is selected from the group consisting of: a small hydrophobic organic molecule, a hydrophilic organic molecule, and an amphiphilic organic molecule.

8. The composition according to claim 4, which can be administered by a route selected from the group consisting of: oral, parenteral, nasal, vaginal, ocular, subcutaneous, intravenous, intramuscular, intradermal, intraperitoneal, intracerebral and buccal route.

9. The composition according to claim 4, wherein said composition form is selected from the group consisting of: a gel, an emulsion, micelles, nanoparticles, microparticles, a powder and a film.

10. The composition according to claim 4, wherein said composition is a colloidal suspension of nanoparticles, microparticles, or micelles of polyamino acids, in an aqueous phase.

11. The composition according to claim 4, wherein said composition is in the form of a solution in a biocompatible solvent that is capable of being injected by the subcutaneous or intramuscular route or into a tumor.

12. The homopolyamino acid according to claim 1, having one of the general formulae (I) or (II), wherein n+m varies from 20 to 300.

13. The homopolyamino acid according to claim 1, having the general formula (III), wherein n varies from 20 to 300.

14. The homopolyamino acid according to claim 1, wherein said homopolyamino acid has a molecular weight between 5000 and 40,000 glmol.

15. The homopolyamino acid according to claim 1, wherein $R^4$ is a metal cation selected from the group consisting of sodium, potassium, calcium, and magnesium.

16. The homopolyamino acid according to claim 1, wherein $R^4$ is an organic cation selected from the group consisting of cations based on amine, cations based on oligoamine, cations based on polyamine, cations based on polyethylenimine, cations based on amino acid(s), and cationic polyamino acids.

17. The homopolyamino acid according to claim 1, wherein $R^4$ is a cation based on lysine or arginine.

18. The homopolyamino acid according to claim 1, wherein $R^4$ is a cationic polyamino acid selected from the group consisting of polylysine and oligolysine.

* * * * *